United States Patent
Nibhanipudi

(10) Patent No.: US 10,583,264 B2
(45) Date of Patent: Mar. 10, 2020

(54) HIGH FLOW OF WARM HUMIDIFIED OXYGEN

(71) Applicant: Kumara Venkatanarayana Nibhanipudi, Scarsdale, NY (US)

(72) Inventor: Kumara Venkatanarayana Nibhanipudi, Scarsdale, NY (US)

(*) Notice: Subject to any disclaimer, the term of this patent is extended or adjusted under 35 U.S.C. 154(b) by 477 days.

(21) Appl. No.: 15/177,580

(22) Filed: Jun. 9, 2016

(65) Prior Publication Data

US 2017/0165448 A1  Jun. 15, 2017

(30) Foreign Application Priority Data

Jun. 9, 2015 (IN) .......................... 2887/CHE/2015

(51) Int. Cl.
| | | |
|---|---|---|
| *A61M 16/10* | (2006.01) | |
| *A61M 16/06* | (2006.01) | |
| *A61M 16/12* | (2006.01) | |
| *A61M 16/08* | (2006.01) | |
| *A61M 16/16* | (2006.01) | |

(52) U.S. Cl.
CPC ........ *A61M 16/10* (2013.01); *A61M 16/0666* (2013.01); *A61M 16/0672* (2014.02); *A61M 16/0833* (2014.02); *A61M 16/109* (2014.02); *A61M 16/1075* (2013.01); *A61M 16/12* (2013.01); *A61M 16/16* (2013.01); *A61M 16/06* (2013.01); *A61M 2202/0208* (2013.01); *A61M 2210/0618* (2013.01)

(58) Field of Classification Search
CPC .. A61M 16/00; A61M 16/06; A61M 16/0666; A61M 16/0672; A61M 16/10; A61M 16/1005; A61M 16/104; A61M 16/1075; A61M 16/108; A61M 16/1085; A61M 16/109; A61M 16/1095; A61M 16/12; A61M 16/16; A61M 16/18; A61M 16/0833
See application file for complete search history.

(56) References Cited

U.S. PATENT DOCUMENTS

| | | | | |
|---|---|---|---|---|
| 5,357,945 | A * | 10/1994 | Messina ................. | A61M 11/06 128/200.14 |
| 2004/0081624 | A1* | 4/2004 | Nguyen ............... | A61K 9/0078 424/44 |
| 2004/0154617 | A1* | 8/2004 | Enk ........................ | A61M 11/06 128/203.12 |
| 2008/0210242 | A1* | 9/2008 | Burk ..................... | A61M 16/06 128/206.21 |

(Continued)

OTHER PUBLICATIONS

Nibhanipudi, Kumara et al. "Beneficial Effects of Warmed Humidified Oxygen Combined with Nebulized Albuterol and Ipratropium in Pediatric Patients with Acute Exacerbation of Asthma in Winter Months", The Journal of Emergency Medicine, vol. 37, No. 4, Dec. 4, 2008, pp. 446-449.*

(Continued)

*Primary Examiner* — Colin W Stuart
(74) *Attorney, Agent, or Firm* — Blue Filament Law PLLC

(57) ABSTRACT

The present invention relates to the administration of warm humidified oxygen to patients suffering with breathing problems. The present invention more specifically relates to the high flow of warm humidified oxygen to patients suffering with breathing problems or suffering with asthma.

18 Claims, 3 Drawing Sheets

(56) References Cited

U.S. PATENT DOCUMENTS

| | | | |
|---|---|---|---|
| 2010/0089395 A1* | 4/2010 | Power | A61M 15/0085 |
| | | | 128/203.15 |
| 2012/0216806 A1* | 8/2012 | Rookard | A61M 16/06 |
| | | | 128/203.29 |
| 2014/0107517 A1* | 4/2014 | Hussain | A61M 16/0672 |
| | | | 600/532 |

OTHER PUBLICATIONS

Fleisher, Gary R. et al. Textbook of Pediatric Emergency Medicine, 5th Edition, Lippincott Williams & Wilkins, May 28, 2005, pp. 131-132.

* cited by examiner

HIGH FLOW OF WARM HUMIDIFIED OXYGEN

FIELD OF INVENTION

The present invention relates to the administration of warm humidified oxygen to patients suffering with breathing problems. The present invention more specifically relates to the high flow of warm humidified oxygen to patients suffering with breathing problems or suffering with asthma.

BACKGROUND OF INVENTION

Asthma is a reversible bronchoconstriction along with mucosal edema. Asthma is a common chronic inflammatory disease of the airways characterized by variable and recurring symptoms, reversible airflow obstruction and bronchospasm. Common symptoms include wheezing, coughing, chest tightness, and shortness of breath.

Asthma is thought to be caused by a combination of genetic and environmental factors. Its diagnosis is usually based on the pattern of symptoms, response to therapy over time and spirometry. It is clinically classified according to the frequency of symptoms, forced expiratory volume in one second (FEV1), and peak expiratory flow rate. Asthma may also be classified as atopic (extrinsic) or non-atopic (intrinsic) where atopy refers to a predisposition toward developing type 1 hypersensitivity reactions.

The usual management is to administer inhaled bronchodilators with oxygen at FiO2 (4 to 6 litres). Treatment of acute symptoms is usually with an inhaled short-acting beta-2 agonist (such as salbutamol) and oral corticosteroids. Long-acting beta agonists (LABA) or antileukotriene agents may be used in addition to inhaled corticosteroids if asthma symptoms remain uncontrolled.

Normal cellular function depends upon a continuous supply of oxygen. Inhaled oxygen diffuses across the alveolar-capillary membrane and into the pulmonary capillary blood. The partial pressure for oxygen in the alveoli (approximately 150 mmHg breathing room air at sea level) is greater than in mixed venous blood (40 mmHg) and in the mitochondria (<10 mmHg). This gradient maintains the arterial oxygen tension ($PaO_2$) and is largely the driving force for oxygen delivery to cells.

Oxygen diffuses into the blood where it is predominantly bound to haemoglobin in red blood cells, with a small proportion being dissolved in plasma. The relationship between $PaO_2$ and haemoglobin is described by the curvilinear oxyhaemoglobin dissociation curve. At a $PaO_2$ above 90 mmHg, the curve is nearly flat, and haemoglobin is almost completely saturated. At lower values of $PaO_2$, the curve falls steeply, promoting release of oxygen to the tissues.

Oxygen affinity, which refers to the ability of haemoglobin to bind or release oxygen, is modulated by pH, $CO_2$ (in part independent of pH), 2,3-diphosphoglycerate (DPG), temperature, and foetal haemoglobin. Lower pH, higher $CO_2$, increased temperature, and a decreased proportion of foetal haemoglobin reduce oxygen affinity. These shifts in affinity promote oxygen uptake in the pulmonary capillaries and release into the tissues.

There are a variety of non-invasive ways in which respiratory support can be provided to preterm infants with apnoea or parenchymal lung disease. These include oxygen via a head box or nasal cannula, nasal continuous positive airways pressure (CPAP) and nasal intermittent positive pressure ventilation (NIPPV).

High flow nasal cannulae (HFNC) are small, thin, tapered cannulae used to deliver oxygen or blended oxygen and air at flow rates of >1 L/min. HFNC can be used to provide high concentrations of oxygen and may deliver positive end-expiratory pressure.

Humidified High-Flow (HHF) oxygen/air is a form of respiratory support in preterm infants where their breathing is spontaneous. It is air-oxygen flow (via blender) of 1-6 L/min via the Fisher & Paykel humidifier. HHF is to be commenced at a flow rate of 5 L/min and can be increased to 6 L/min after consultation with registrar/NS-ANP. Potential for asynchrony in breathing may result in the infant becoming tired over long periods; therefore, good assessment of work of breathing is required. Potential for nasal erosion (although less than with HCPAP) remains.

A non-rebreather mask, or NRB, is a device used in medical emergencies that requires oxygen therapy. An NRB requires that the patient can breathe unassisted, but unlike low flow nasal cannula, the NRB allows for the delivery of higher concentrations of oxygen.

Heated Humidified High Flow (HHHF) Therapy is a type of respiratory support is a method of delivering a high minute flow of medical gas to a patient through an interface intended to provide respiratory support; typically a nasal cannula. The applied gas is heated to a set temperature and humidified, targeting ideal body saturation vapor pressure.

Nasal cannula used for medical gas delivery are usually limited to delivery of 1-6 litres of flow per minute. The percent oxygen inhaled by the patient (FiO2), usually ranges roughly from 24% to 35% as the pure oxygen delivered from the cannula is diluted by entrainment of ambient air (21% oxygen). Flow rates for delivery of oxygen using typical nasal cannula are limited because medical oxygen is anhydrous, and when delivered from a pressurized source the gas cools as it expands with the drop to atmospheric pressure. Delivery of cold dry gas is irritating to the respiratory mucosa, can cause drying and bleeding of the nasal mucosa and can increase metabolic demand by cooling the body.

It can be comprehended from the prior art that there are several methods for increasing flow of oxygen using different techniques and devices. However, each arrangement has its own disadvantages.

OBJECTIVE OF THE INVENTION

The objective of the present invention is to administer combination of nebulized anti-asthmatic drugs with warmed humidified oxygen.

Another objective of the present invention is to administer combination nebulized anti-asthmatic drug with warmed humidified oxygen using a nasal cannula and nebuliser face mask.

SUMMARY OF THE INVENTION

The present invention relates to the method of administration of a combination of nebulized anti-asthmatic drugs with warmed humidified oxygen.

Another embodiment of the present invention relates to the method of administration of a combination of nebulized anti-asthmatic drugs with warmed humidified oxygen using nasal cannula and nebuliser face mask.

Another embodiment of the present invention relates to the method of administration of a combination of bronchodilators with warmed humidified oxygen using nasal cannula and nebuliser face mask.

Yet another embodiment of the present invention relates to the method of administration of a combination of albuterol and ipratropium with warmed humidified oxygen using nasal cannula and nebulizer face mask.

BRIEF DESCRIPTION OF FIGURES

The following figure has been provided along with the detailed description of the present invention by way of illustration only for a better comprehension of the procedure, wherein.

DETAILED DESCRIPTION OF THE INVENTION

Figure 1:
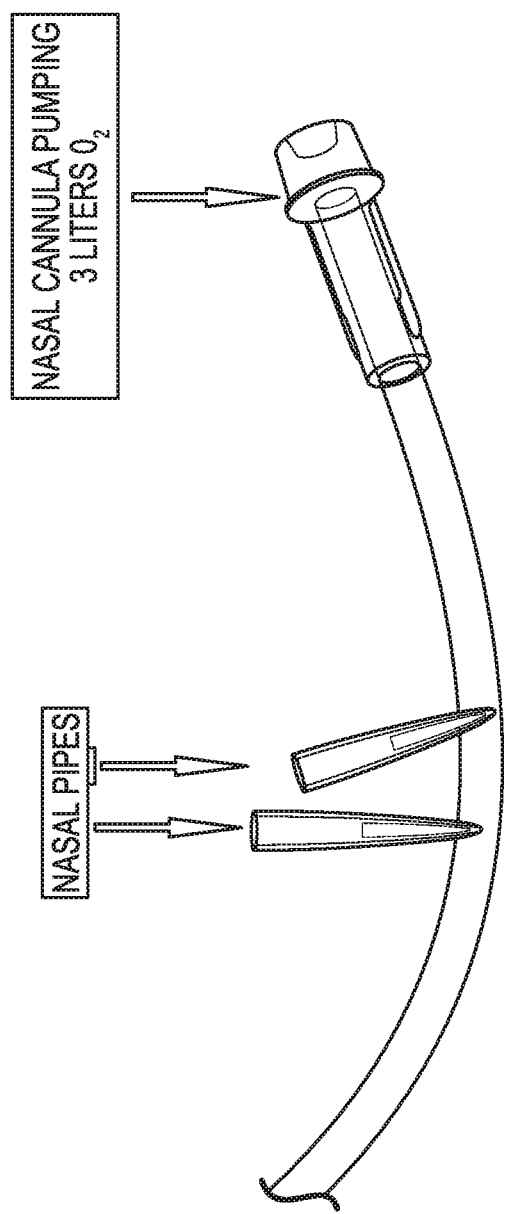
FIG. 1: Nasal Cannula with nasal pipes for administering oxygen.
Figure 2:
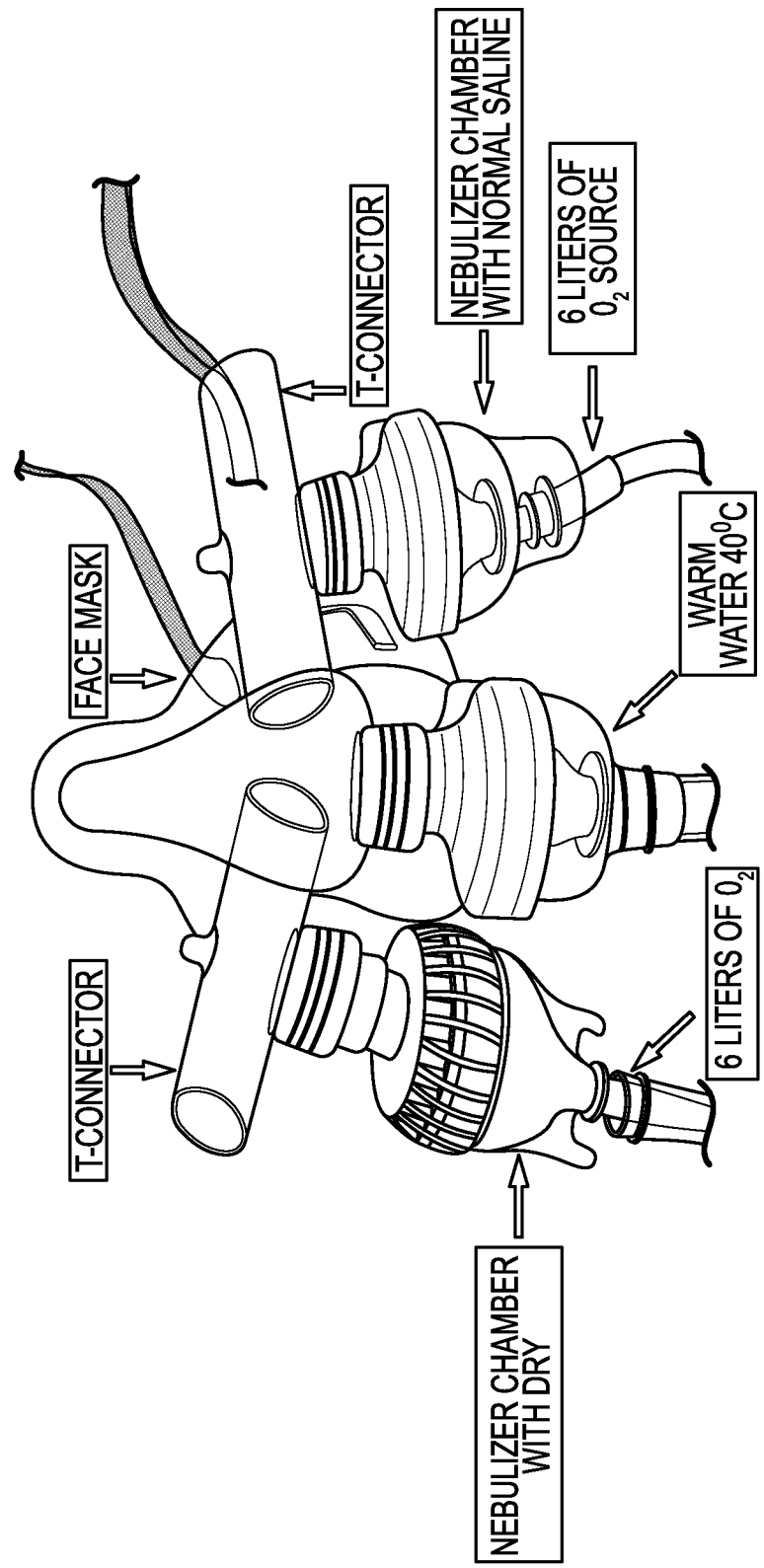
FIG. 2: Nebuliser face mask with two T-connectors and a connector for supplying warm air.
Figure 3:
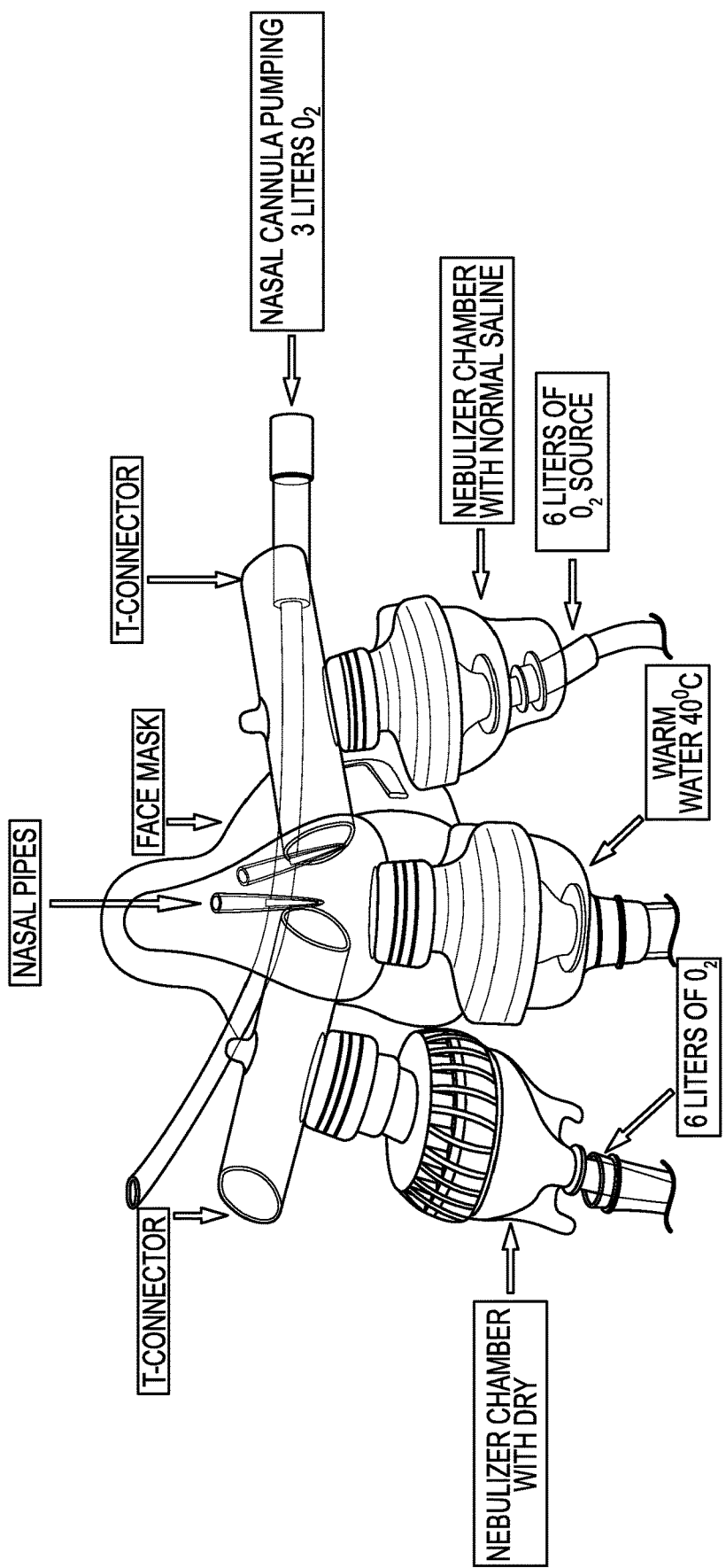
FIG. 3: Nasal Cannula with nasal pipes for administering oxygen and Nebuliser face mask with two T-connectors and a connector for supplying warm air.

The present invention relates to the method of administration of a combination of nebulized anti-asthmatic drugs with warmed humidified oxygen.

The present invention relates to the method of administration of a combination of nebulized anti-asthmatic drugs with warm humidified oxygen using nasal cannula and nebuliser face mask.

The present invention relates to the method of administration of a combination of nebulized combination of albuterol and ipratropium with warm humidified oxygen using nasal cannula and nebuliser face mask.

The present invention relates to the method of administering of warm humidified high-flow of oxygen (15 litres of $O_2$ per minute) which will cause the bronchodilators to get deeper into the airways and cause more effective reduction in bronchoconstriction.

The bronchodilators that can be used according to the warm humidified high-flow of oxygen therapy include both short-acting bronchodilators—which are used as short-term relief from sudden, unexpected attacks of breathlessness and long-acting bronchodilators—which have longer-lasting effects and, if used regularly, can not only help control breathlessness in asthma and COPD, but also increase the effectiveness of corticosteroids in asthma.

The bronchodilators used according to the present invention include Beta-2 agonists such as albuterol, salbutamol, salmeterol, formoterol and vilanterol.

The bronchodilators used according to the present invention include anticholinergics (also known as antimuscarinics)—such as ipratropium, tiotropium, aclidinium and glycopyrronium.

The present invention relates to the utilization of humidified high-flow of oxygen which can comfortably deliver optimal humidified high-flow oxygen and drug therapy via nasal cannula and nebuliser face mask at flow rates of up to 15 litres/minute.

Description of the Device and Method of Administering the Bronchodilator:

The set-up requires three oxygen sources using a Nasal Cannula and Face Mask. Using the first oxygen source, 3 litres per minute of $O_2$ is administered via nasal cannula fitting to both nares of the nose. The face mask which contains three apertures is placed on the face over the nasal cannula. The two apertures on the sides of the mask are fitted with a T-connector.

One end of the horizontal portion of first T-connector is inserted into one of the apertures of the face mask, the vertical portion of the T-connector is connected to a nebulizer chamber containing an anti-asthmatic drug.

This nebulizer chamber is connected via plastic tubing to the second oxygen source to administer 6 litres per minute of $O_2$.

The second T-connector is inserted into second aperture of the face mask, which is connected to a third oxygen source using a nebuliser chamber to administer another 6 litres per minute of $O_2$.

The middle aperture is connected to a portable nebuliser. The portable nebuliser chamber is used to supply warm humidified air. The warm humidified air can be supplied by different methodologies. For instance, 5 cc of sterile water is added to a sterile cup which is heated in a microwave oven for 2 minutes. The temperature of the water is checked by using a thermometer. If the temperature of the water is higher than 40° C. then sterile water of room temperature is added to adjust the temperature. 3 cc of this heated water is added to the nebuliser chamber.

The ease of the equipment used as per the present invention gives convenience using in hospital or at home. The oxygen is saturated with water vapour at around body temperature (~40° C.) allowing flow to be well tolerated first.

The present invention specifically shows that warmed humidified oxygen given along with the combination of nebulized albuterol and ipratropium is more beneficial for paediatric patients having an acute exacerbation of bronchial asthma in the winter months when compared to nebulized albuterol alone with warmed humidified oxygen, nebulized albuterol alone with room temperature humidified oxygen, or a combination of nebulized albuterol and ipratropium with room temperature humidified oxygen.

Advantages of the Present Invention:
  More effective resolution and significant improvement of clinical symptoms observed in asthma severity.
  Decreased stay in the emergency room and also decrease in hospitalization.

I claim:

1. A method for treating asthma comprising:
   placing a nasal cannula on a patient;
   placing a nebulizer face mask on the patient over the nasal cannula, the nebulizer face mask having a first side aperture, a second side aperture, and a central aperture;
   administering oxygen through the nebulizer face mask from a first oxygen source fluidly connected to a first nebulizer chamber, the first nebulizer chamber fluidly connected to the nebulizer face mask by a first T-connector, the first T-connector having a first branch inserted into the first side aperture of the nebulizer face mask, a second branch vented to the atmosphere, and a third branch connected to the first nebulizer chamber;
   administering oxygen through the nebulizer face mask from a second oxygen source fluidly connected to a second nebulizer chamber, the second nebulizer chamber fluidly connected to the nebulizer face mask by a second T-connector, the second T-connector having a first branch inserted into the second side aperture of the nebulizer face mask, a second branch vented to the atmosphere, and a third branch connected to the second nebulizer chamber;
   administering oxygen through the nasal cannula from a third oxygen source;
   providing an anti-asthmatic drug in the first nebulizer chamber or the second nebulizer chamber;

nebulizing the anti-asthmatic drug;
supplying warm humidified air to the nebulizer face mask from a third nebulizer chamber fluidly connected to the nebulizer face mask at the central aperture of the nebulizer face mask;
combining the nebulized anti-asthmatic drug with the warm humidified air and the oxygen being administered from the first oxygen source and the second oxygen source; and
wherein the oxygen from the third oxygen source and the combined nebulized anti-asthmatic drug, warm humidified air, and the oxygen from the first oxygen source and the second oxygen source are administered at a flow rate of up to 15 liters per minute total.

2. The method of claim 1, wherein the nebulized anti-asthmatic drug comprises a combination of bronchodilators.

3. The method of claim 2, wherein the combination of bronchodilators comprises a Beta-2 agonist bronchodilator and an anticholinergic bronchodilator.

4. The method of claim 3, wherein the Beta-2 agonist bronchodilator is albuterol and the anticholinergic bronchodilator is ipratropium.

5. The method of claim 1, further comprising adding 5 cc of 40° C. heated water into the third nebulizer chamber.

6. The method of claim 5, wherein the heated water humidifies and produces the warm humidified air that is supplied from the third nebulizer chamber.

7. The method of claim 1, wherein administering oxygen from the first oxygen source comprises administering 6 liters of oxygen per minute.

8. The method of claim 1, wherein administering oxygen from the second oxygen source comprises administering 6 liters of oxygen per minute.

9. The method of claim 1, wherein administering oxygen from the third oxygen source comprises administering 3 liters of oxygen per minute.

10. The method of claim 1, wherein the method is used to treat acute exacerbation of asthma in pediatric patients.

11. The method of claim 1, wherein administering oxygen from the first oxygen source is done at a flow rate of 6 liters per minute, administering oxygen from the second oxygen source is done at a flow rate of 6 liters per minute, and administering oxygen from the third oxygen source is done at a flow rate of 3 liters per minute.

12. The method of claim 1, further comprising:
operably connecting the first nebulizer chamber to the nebulizer face mask by fitting a horizontal portion of the first T-connector into the first side aperture and fitting a vertical portion of the first T-connector to the first nebulizer chamber operatively connected to the first oxygen source;
operably connecting the second nebulizer chamber to the nebulizer face mask by fitting a horizontal portion of the second T-connector into the second side aperture and fitting a vertical portion of the second T-connector to the second nebulizer chamber operatively connected to the second oxygen source; and
operably connecting the third nebulizer chamber to the central aperture.

13. The method of claim 1, wherein the third nebulizer chamber is part of a portable nebulizer.

14. A method for treating asthma comprising:
fitting a nasal cannula on a patient, the nasal cannula being operatively connected to a cannula oxygen source;
administering oxygen from the cannula oxygen source;
fitting a nebulizer face mask on the patient over the nasal cannula, the nebulizer face mask having a first side aperture, a second side aperture, and a central aperture;
inserting a first horizontal portion of a first T-connector into the first side aperture, a second horizontal portion of the first T-connector venting to the atmosphere;
connecting a vertical portion of the first T-connector to a first nebulizer chamber containing an anti-asthmatic drug and operatively connecting the first nebulizer chamber to a first oxygen source;
inserting a first horizontal portion of a second T-connector into the second side aperture, a second horizontal portion of the second T-connector venting to the atmosphere;
connecting a vertical portion of the second T-connector to a second nebulizer chamber and operatively connecting the second nebulizer chamber to a second oxygen source;
operatively connecting a third nebulizer chamber to the central aperture;
adding heated water into the third nebulizer chamber;
administering oxygen from the first oxygen source and combining it with the anti-asthmatic drug in the first nebulizer chamber;
administering oxygen from the second oxygen source;
administering warm humidified air from the third nebulizer chamber;
wherein administering oxygen from the first oxygen source, the second oxygen source, and the cannula oxygen source is done at a combined flow rate of up to 15 liters per minute.

15. The method of claim 14, wherein administering oxygen from the first oxygen source is done at a flow rate of 6 liters per minute, administering oxygen from second oxygen source is done at a flow rate of 6 liters per minute, and administering oxygen from the cannula oxygen source is done at a flow rate of 3 liters per minute.

16. The method of claim 14, wherein the nebulized anti-asthmatic drug comprises a bronchodilator.

17. The method of claim 16, wherein the bronchodilator is a Beta-2 agonist bronchodilator or an anticholinergic bronchodilator.

18. The method of claim 16, wherein the bronchodilator comprises a combination of albuterol and ipratropium.

* * * * *